US012636496B2

(12) United States Patent
Chen et al.

(10) Patent No.: US 12,636,496 B2
(45) Date of Patent: May 26, 2026

(54) PHOTOVOLTAIC RETINAL PROSTHESIS WITH OPTICALLY CONFIGURABLE CONFINEMENT OF ELECTRIC FIELD

(71) Applicant: The Board of Trustees of the Leland Stanford Junior University, Stanford, CA (US)

(72) Inventors: Zhijie Chen, Stanford, CA (US); Daniel V. Palanker, Sunnyvale, CA (US); Bingyi Wang, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 326 days.

(21) Appl. No.: 18/271,450

(22) PCT Filed: Mar. 16, 2022

(86) PCT No.: PCT/US2022/020498
§ 371 (c)(1),
(2) Date: Jul. 8, 2023

(87) PCT Pub. No.: WO2022/212053
PCT Pub. Date: Oct. 6, 2022

(65) Prior Publication Data
US 2024/0058607 A1 Feb. 22, 2024

Related U.S. Application Data

(60) Provisional application No. 63/168,786, filed on Mar. 31, 2021.

(51) Int. Cl.
*A61N 1/36* (2006.01)
*A61N 1/05* (2006.01)

(52) U.S. Cl.
CPC ....... *A61N 1/36046* (2013.01); *A61N 1/0543* (2013.01)

(58) Field of Classification Search
CPC .......................... A61N 1/36046; A61N 1/0543
See application file for complete search history.

(56) References Cited

U.S. PATENT DOCUMENTS 10,980,997 B2    4/2021   Deterre
2022/0176105 A1*  6/2022   Palanker ............. A61N 1/3616

OTHER PUBLICATIONS

Palanker et al. Design of a high-resolution optoelectronic retinal prosthesis. J. Neural Eng. 2025, Mar;2(1):S105-20. doi: 10.1088/1741-2560/2/1/012.

(Continued)

*Primary Examiner* — Richard G Louis
(74) *Attorney, Agent, or Firm* — LUMEN PATENT FIRM

(57) ABSTRACT

Photovoltaic retinal prosthesis is provided with optically configurable confinement of electrical field. A video stream is projected onto a retinal implant. An array of photovoltaic pixels is configured to provide retinal stimulus responsive to the video stream. The photovoltaic pixels have a common return electrode. Each pixel has an active electrode that is coupled to retinal tissue via a capacitive interface or a faradaic interface. Each pixel includes photodiode(s) connected in series between the common return electrode and the corresponding active electrode. The projected video stream is configured based on a source video stream such that one or more pixels of the retinal implant that will be dark in a next frame of the projected video stream are optically preconditioned (pre-charged) by the projected video stream during the previous frame to become sufficiently conductive to act as transient local return electrodes during the next frame of the projected video stream.

11 Claims, 10 Drawing Sheets

(56) References Cited

OTHER PUBLICATIONS

Boinagrov et al. Photovoltaic Pixels for Neural Stimulation: Circuit models and performance. IEEE Trans. Biomed. Circuits and Systems 10(1) 20216, 85-97.

Loudin et al. Optoelectronic retinal prosthesis: system design and performance. J. Neural Eng. 4(2007) S72-S84.

Loudin et al. Photovoltaic Retinal Prosthesis. 2011 Proc. SPIE vol. 788513: 1-13.

Loudin et al. High resolution optoelectronic retinal prosthesis. 2009 Proc. SPIE vol. 7163: 1-11.

* cited by examiner

Near-infrared beam

Subretinal implant camera mirror retina projector

PHOTOVOLTAIC RETINAL PROSTHESIS WITH OPTICALLY CONFIGURABLE CONFINEMENT OF ELECTRIC FIELD

CROSS-REFERENCE TO RELATED APPLICATIONS

This application is a 371 of PCT application PCT/US2022/020498 filed Mar. 16, 2022. PCT application PCT/US2022/020498 claims the benefit of U.S. Provisional application 63/168,786 filed Mar. 31, 2021.

This invention was made with Government support under contract FA9550-19-1-0402 awarded by the Air Force Office of Scientific Research, contract W81XWH-19-1-0738 awarded by the Department of Defense, contract EY027786 awarded by the National Institutes of Health. The Government has certain rights in the invention.

FIELD OF THE INVENTION

The invention relates to photovoltaic retinal prostheses.

BACKGROUND OF THE INVENTION

Retinal degenerative diseases, such as age-related macular degeneration (AMD) and retinitis pigmentosa, are a leading cause of untreatable visual impairment and legal blindness. Despite the irreversible loss of photoreceptors, the inner retinal neurons survive to a large extent. Electrical stimulation of the secondary retinal neurons, primarily the bipolar cells, elicits visual percepts, hence enabling electronic restoration of sight. AMD patients with a photovoltaic subretinal implant PRIMA (Pixium Vision, Paris, France) having bipolar pixels of 100 μm demonstrated prosthetic letter acuity of 1.17±0.13 pixels, corresponding to the Snellen range of 20/460-20/565. Even though this is a very exciting proof of concept, for a wide adoption of this approach by AMD patients, prosthetic acuity should certainly exceed their remaining peripheral vision, which is typically no worse than 20/400. Sampling limit for acuity of 20/200 corresponds to 50 μm pixels and 20/100- to 25 μm.

Like with natural vision, prosthetic visual acuity is fundamentally limited not only by the spatial resolution (i.e. pixel size), but also by contrast of the stimulation patterns, which is affected by crosstalk between the neighboring electrodes. Lateral spread of the electric field can be confined by local return electrodes in each pixel, as in the PRIMA implant, but scaling down such bipolar pixels is difficult because penetration depth of electric field in tissue is also constrained to about a pixel radius. As a result, retinal stimulation threshold in such geometry rapidly increases with the decreasing pixel size, and it exceeds the safe charge injection limit for even one of the best electrode materials (SIROF) with pixels below 40 μm in size.

One approach to overcome this problem is based on elevation of the return electrode to the top of the inner nuclear layer using 3-D honeycomb-shaped array, thereby orienting the electric field vertically within the wells. This arrangement decouples the field penetration depth from the pixel width and greatly reduces the stimulation threshold because the vertical field matches the orientation of the bipolar cells in the retina. Although initial animal studies have shown promising results with retinal migration into the subretinal wells, functionality of the migrated neurons into 3-D arrays remains to be confirmed. Besides, the fabrication process of the honeycomb structures with a local return electrode is far from trivial, and needs to be further developed.

SUMMARY OF THE INVENTION

Spatial resolution of a retinal prosthesis is limited by the pixel size and by crosstalk from the neighboring electrodes. Local return electrodes in bipolar pixels help reduce the cross-talk, but they over-constrain the electric field penetration into the tissue and thus limit the efficacy of neural stimulation. Charging the active electrodes, which are capacitively or faradaically coupled to the electrolyte, as well as presence of the electric field generated by the neighboring active electrodes, elevate the electric potential on active electrode. Increased potential across a photodiode in the photovoltaic pixel makes it more conductive, effectively transforming it into a transient return electrode. Therefore, pre-charging the active electrodes makes them effective return electrodes for the next pulse if they become dark pixels in the next image. The distance between the active electrode and the return electrode defines the penetration depth of the electric field into tissue. Such preconditioning of the pixels to become transient returns in the next image frame enables flexible control of the lateral and axial confinement of electric field in tissue by spatiotemporal control of the images projected onto the photovoltaic array. It allows optimization of the stimulation depth and lateral selectivity in every patient, depending on the retinal thickness and its proximity to the implant.

Alternatively, photovoltaic pixels can be turned into transient returns by optically controlling the discharge with photosensitive transistors responding to a different range of wavelengths. These could be phototransistors or metal-oxide-semiconductor field-effect transistors (MOSFETs) gated by secondary photodiodes. Such separate optically-controlled elements can help discharge the active electrodes in the pixels faster and also enable optimization of the current steering in the retina to generate specified electric fields.

In first embodiment, the invention is a method of providing illumination to a photovoltaic retinal prosthesis. The method distinguishes projecting a video stream onto a retinal implant. The retinal implant includes an array of photovoltaic pixels configured to provide retinal stimulus responsive to the video stream. The array of photovoltaic pixels has a common return electrode. Each pixel has an active electrode that is coupled to retinal tissue via a capacitive interface or a faradaic interface. Each pixel includes one or more photodiodes connected in series between the common return electrode and the corresponding active electrode. The method further distinguishes configuring the projected video stream based on a source video stream such that one or more pixels of the retinal implant that will be dark in a next frame of the projected video stream are optically preconditioned (pre-charged) by the projected video stream to become sufficiently conductive, so they can act as transient local return electrodes during the next frame of the projected video stream.

In a further embodiment of the method, the transient local return electrodes are preconditioned to reach a bias voltage in a range of 0.2 V to 0.7 V per photodiode by illumination from the projected video stream.

More optimally, the transient local return electrodes are preconditioned to reach the bias voltage in the range of 0.3 V to 0.6 V per photodiode.

In yet another embodiment, the method distinguishes that the image processing duration for pre-conditioning and stimulation is no longer than a frame duration of the source video stream.

In still another embodiment, the method distinguishes a preconditioning algorithm which defines a polarity and an amplitude of the current at each electrode, and is optimized under a minimum-mean-square-error criterion to approximate a target electric field in a biological tissue.

In a second embodiment, the invention is a retinal prosthesis system having a near-the-eye display for a video stream projection onto a retinal implant. The retinal implant has photovoltaic pixels which convert near-infrared light (e.g. 850-915 nm) projected from the display into an electric current flowing through a biological tissue to stimulate retinal neurons. Each pixel in the retinal implant has one or more photodiodes connected in series between an active electrode and a return electrode. The active and return electrodes are coupled to an electrolyte of the biological tissue via a capacitive interface or a faradaic interface, and the return electrodes of the pixels are connected together. A sequence of images in the video stream projected by the near-the-eye display onto the retinal implant is designed to optically precondition designated pixels to become sufficiently conductive to serve as transient return electrodes by accumulating a bias voltage at an electrode-electrolyte interface in these pixels.

In a further embodiment of the system, the photodiodes are made of crystalline silicon and wherein the bias voltage is in the range of 0.2-0.7 V per photodiode. More optimally, the bias voltage exceeds 0.3V per photodiode.

In yet another embodiment of the system, a penetration depth of an electric field into the retina is optimized for an anatomy of a patient by controlling a distance between illuminated pixels in a current video frame and the pixels preconditioned in previous frames, but not illuminated in the current video frame.

In yet another embodiment of the system, the photovoltaic pixels have one or more optically controlled transistors to regulate a discharge current.

In a third embodiment, the invention is a retinal prosthesis that has an array of photovoltaic pixels configured to provide retinal stimulus responsive to a received video stream. The array of photovoltaic pixels has a common return electrode. Each pixel has an active electrode that is capacitively or faradaically coupled to a retinal tissue. Each pixel includes one or more photodiodes connected in series between the return electrode and the corresponding active electrode. Each pixel further includes an optically controllable conductance element, where illumination of the array of photovoltaic pixels with a secondary illumination pattern selects one or more pixels of the retinal implant to act as local return electrodes by activating corresponding conductance elements. The conductance elements are not sensitive to the NIR light, but are sensitive to a different wavelengths range (e.g. visible wavelengths range). This secondary illumination pattern is delivered at the wavelengths range that affects the conductance elements.

The latter embodiment does not require preconditioning (pre-charging) of the pixels, but rather allows a direct control of the pixels' conductivity using a secondary wavelength of light. This embodiment simplifies the control of the pixels conductivity and thereby simplifies the control of the electric field confinement in the retina.

BRIEF DESCRIPTION OF THE DRAWINGS

(FIG. 4B) Same, but with the photodiodes of the 6 neighboring pixels optically pre-conditioned (pre-charged) to 0.54 V prior to the activation of the central pixel.

In FIG. 6A) side view of the electric potential above the photovoltaic array with 40 μm pixels illuminated by a grating pattern with stripes equal to 1 pixel in width, with preconditioning (solid line) and without it (dash). With preconditioning, contrast between the bright and dark stripes is 100%, but without preconditioning, electric potential above the illuminated stripes is only about 25% higher than above the dark stripes. Such a low contrast precludes the detection of the visual response to alternating gratings in rats.

In FIG. 8A replacing the phototransistor in FIG. 8A with a MOSFET controlled by a secondary photodiode.

DETAILED DESCRIPTION

Figure 1:
FIG. 1 shows according to an exemplary embodiment of the invention a near-the-eye projection system for a retinal prosthesis, including a video camera on augmented-reality glasses, an image processor and a projector, which delivers the images captured by the camera to the retinal implant using near-infrared (e.g. 850-915 nm) light, and a subretinal photovoltaic array.

Photovoltaic retinal prosthesis is activated by near-infra-red (NIR) light projected from the augmented reality glasses (FIG. 1). Images are captured by the camera mounted on the glasses, processed in a pocket computer and projected into the eye using pulsed NIR light. Each pixel of the implant (FIGS. 2A-B) converts this light into pulsed electric current flowing through the retina to stimulate the nearby inner retinal neurons.

Figure 2B:
FIGS. 2A-B show according to an exemplary embodiment of the invention a photovoltaic array with 40 μm pixels (FIG. 2A), connected to a common return electrode in the periphery (1). A higher magnification view of the array (FIG. 2B) demonstrating individual pixels in a hexagonal array with the active electrodes (2) in the center and photosensitive area around them (3).
Figure 2B:
Figure 2A:
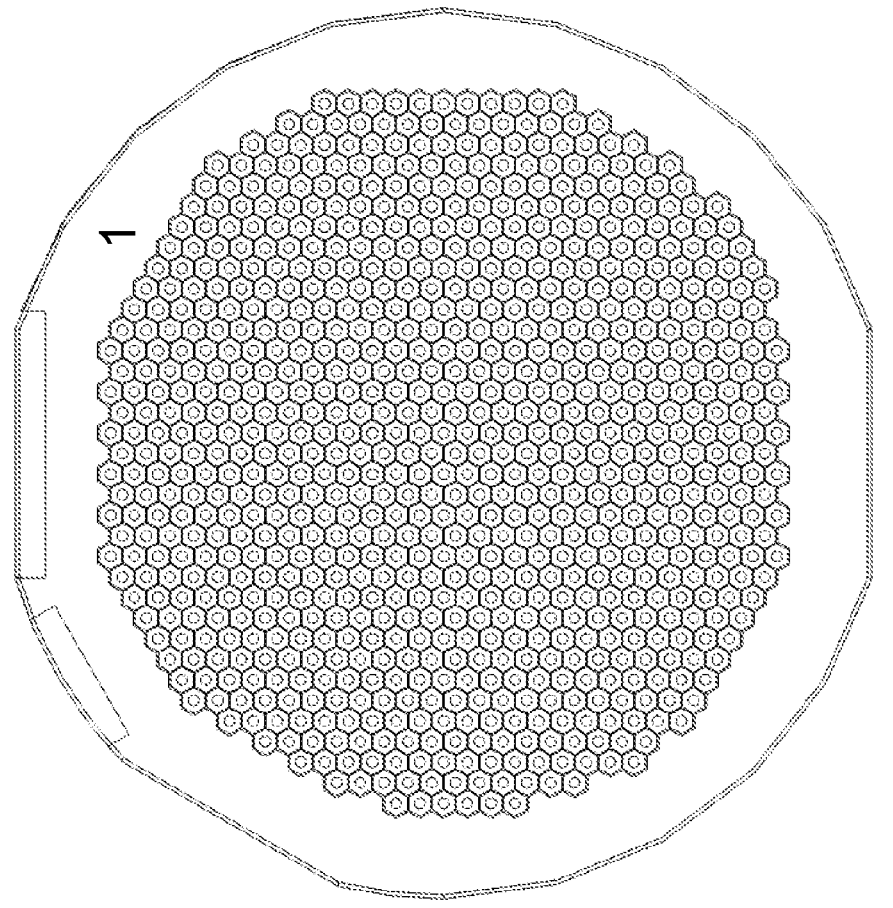

Here, we present an approach to high resolution prosthetic vision with a planar subretinal implant, where the high penetration depth and high contrast of the electric field in tissue are enabled by the spatiotemporal modulation of the photovoltaic pixels, leveraging conductivity of the diodes under forward bias. Accumulation of charge at the electrode-electrolyte interface and coupling of the electric potentials from the neighboring pixels in electrolyte elevate the potential on active electrodes. Since the forward conductance of the photodiode exponentially increases with the electrode potential (FIG. 3), some pixels can become sufficiently conductive and hence be transformed into transient local returns, and thereby help confine the electric field generated by other pixels in the array. Therefore, pre-charging some of the active electrodes makes them effective return electrodes for the next image, if they become dark pixels in the next image projected onto the array. The distance between the active electrode and the return electrode defines the penetration depth of the electric field into tissue. Such preconditioning of the pixels to become transient returns in the next image frame enables flexible control of the lateral and axial confinement of the electric field in tissue by spatiotemporal modulation of the images projected onto the photovoltaic array. It allows optimization of the stimulation depth and lateral selectivity in every patient, depending on the retinal thickness and its proximity to the implant. Such a monopolar photovoltaic array is shown in FIGS. 2A-B. Each pixel has a light-sensitive area (3) connected to the active electrode (2) and to a common return electrode located at the edge of the implant (1).

Figure 7A:
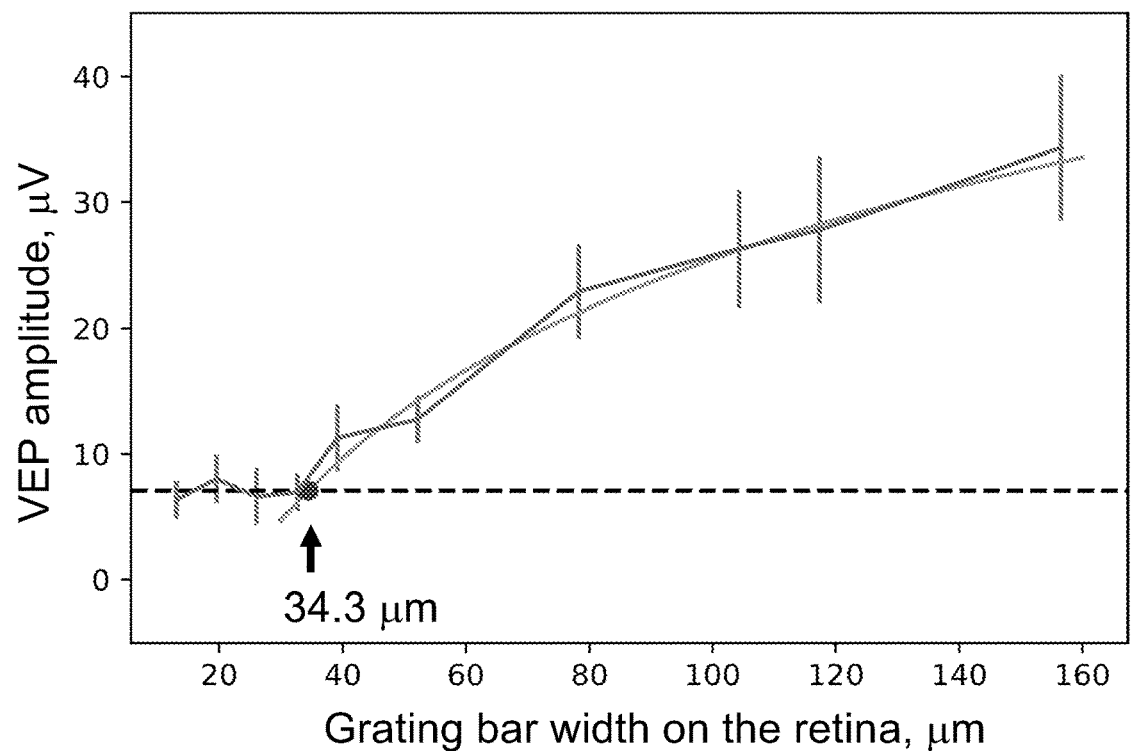
FIGS. 7A-B show according to an exemplary embodiment of the invention amplitude of the visually-evoked potential in response to alternating gratings in rats with photovoltaic arrays having 20 and 40 μm pixels. Alternating grating responses decrease with a decreasing stripe width, and reach the noise level (horizontal line) below the acuity limit. For 40 μm pixels (FIG. 7A), this limit matches the pixel size of 40 μm (pointed by the arrow). For 20 μm pixels (FIG. 7B), the limit is set by the natural spatial resolution in rats, which is about 27 μm (also pointed by the arrow).
Figure 7B:
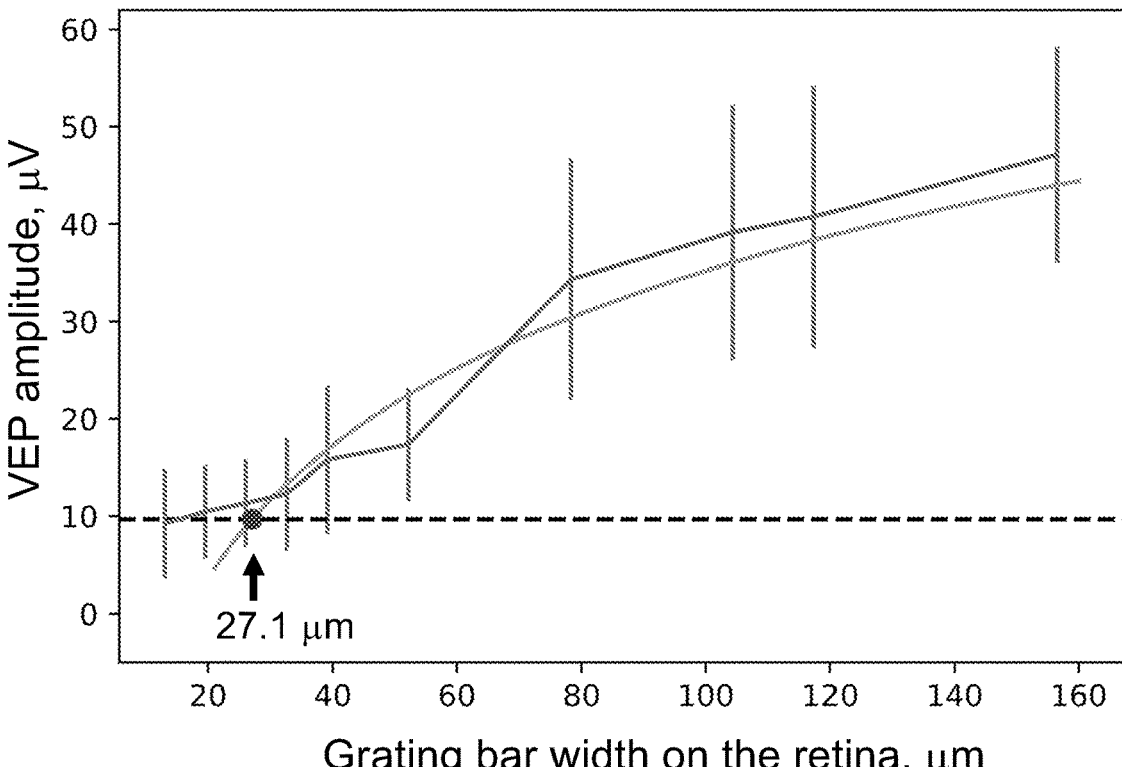

Modeling of such an operation includes (a) characterizing the spatial coupling among pixels using static finite-element modeling, and then (b) computing the photovoltaic circuit dynamics in the multi-dimensional form, from which the potential in the electrolyte is described as a function of space and time. As shown in FIGS. 4A-B, 5 and 6A-B, computational modeling demonstrated that with pre-conditioning, field confinement around the illuminated pixel is much better than without the preconditioning. These results were validated by comparison to the measurements of the electric potential in electrolyte. Most importantly, in-vivo measurements of the grating acuity in animals with 40 µm pixels demonstrated that this approach enables pixel-size limited resolution (FIG. 7A), as predicted by the computational modeling (FIGS. 6A-B), which was not possible with pixels smaller than 55 µm in other configurations. Moreover, with 20 µm pixels, visual acuity in rats is limited by their natural spatial resolution of about 27 (1.2 cpd), as shown in FIG. 7B.

Conductance of a p-n junction exponentially increases with its forward-bias voltage and becomes significant only when the sum of (a) the voltage build-up due to accumulation of charge at the electrode-electrolyte interface and (b) the potential increase due to the current generated by the neighboring pixels in electrolyte exceeds the turn-on voltage of the diode, which is about 0.5V for silicon-based photodiodes. Therefore, once the forward bias drops below the turn-on voltage, further discharge of the electrode becomes inefficient. Shunt resistor in parallel with the photodiode can accelerate the discharge of the active electrode, however, the discharge current will vary in time and depend on the cross-pixel coupling.

Figure 8B:
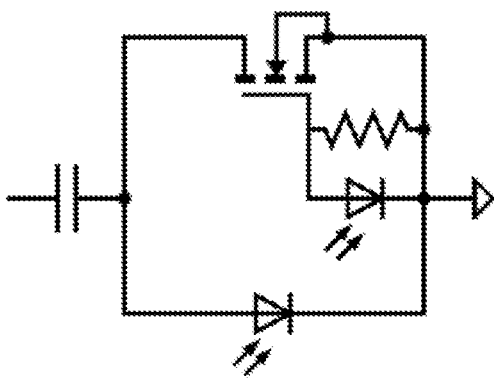
FIGS. 8A-B show according to an exemplary embodiment of the invention in FIG. 8A a circuit diagram of photovoltaic pixels with phototransistors, whose discharge currents can be independently controlled by light of a different wavelength.
Figure 8A:
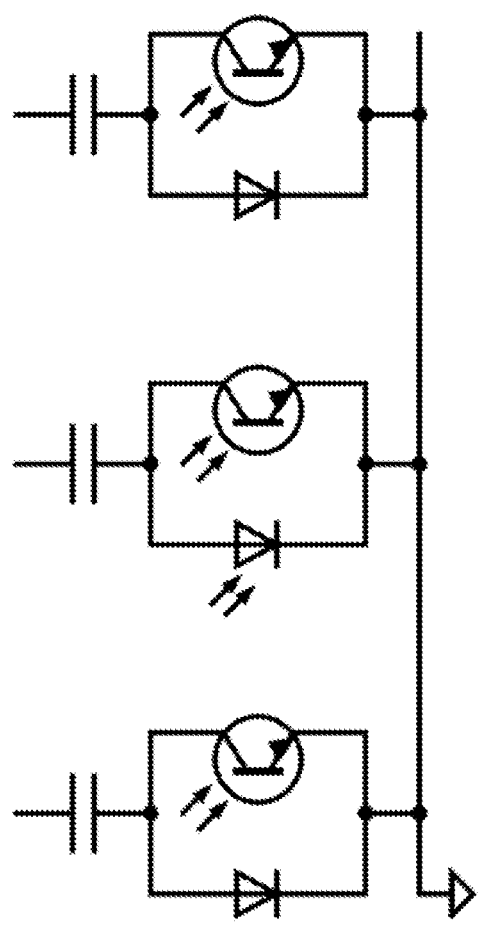
Figure 9:
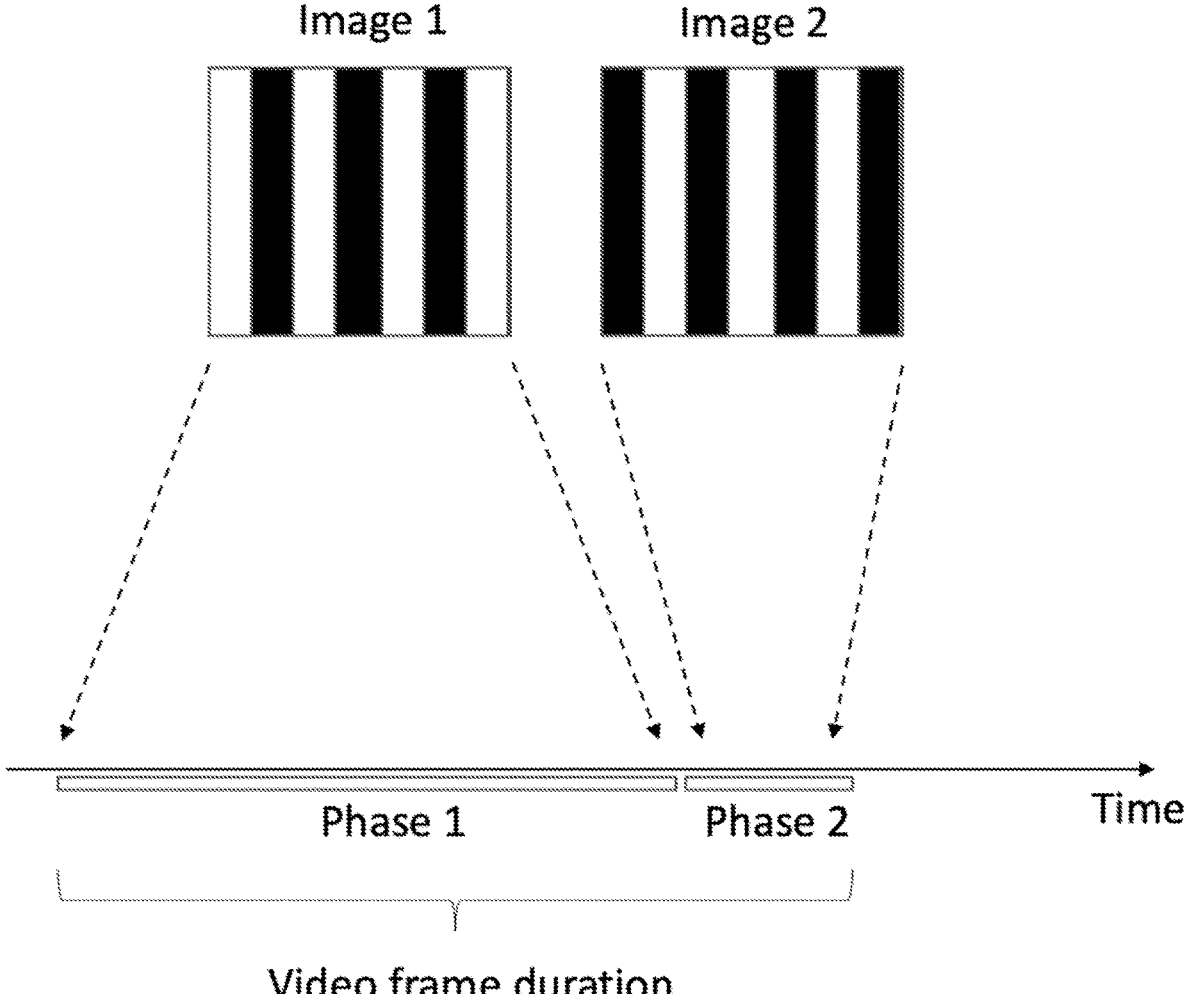
FIG. 9 shows according to an exemplary embodiment of the invention each frame of the video stream is divided into the pre-conditioning phase and a stimulation phase. During the pre-conditioning phase, pixels that will be dark in the stimulation phase are illuminated (image 1) at sub-threshold intensity to accumulate charge at the electrode-electrolyte interface and thereby make these diodes conductive. During the shorter stimulation phase, the bright pixels are illuminated above the stimulation threshold (image 2), while the dark pixels are conductive and hence play a role of the local return electrodes.

In order to provide a more reliable and independent control of the pixel discharge and the transient return, one can integrate the optical control by photosensitive transistors in each pixel responding to a range of wavelengths different than the NIR light used for the primary photodiode. For example, the photovoltaic pixels in FIGS. 4A-B can be substituted with those in FIG. 8A, where each pixel has, in parallel, the primary photodiode and a phototransistor for controlling of the discharge. The phototransistor is protected by a dichroic coating blocking the NIR wavelength used to drive the primary photodiode while passing a secondary wavelength (e.g. visible light). To prevent unintended discharge due to ambient light, this wavelength should be blocked by the glasses. To transform a pixel into a transient return, the phototransistor is turned on by light of the secondary wavelength, and it will conduct the current in the reverse direction, with respect to the photocurrent flow in the primary photodiode. The intensity of the secondary light can be much lower than the primary NIR beam, and the amplitude of the negative current is controlled by the intensity profile of the secondary light. For a higher current gain and larger input resistance, a MOSFET controlled by a secondary photodiode may be used in place of the phototransistor (FIG. 8B).

Optically configuring the negative currents on various pixels enables optimization of the current steering for the field confinement in the retina. To find the optimal currents on each electrode $x=[x_1, x_2, \ldots, x_N]^T$ that generate the targeted electric field $v$, we exploit the linearity of the electric field, and formulate the problem as a minimization of the difference between the actual and the targeted fields under the minimum-mean-square-error (MMSE) criterion:

$$x^* = \operatorname{argmin}_x \|Ux - v\|^2, \tag{1}$$

where U is the transform matrix from the currents at each electrode to the electric field in the retina. The solution to (1) can be efficiently calculated in real time with one step of matrix-vector multiplication. However, the solution may involve currents of large amplitudes that exceed the safety limits of the charge injection of the electrodes. We present the method of using the L-2 regularization in the optimization to avoid excessively large amplitude of currents:

$$x^* = \operatorname{argmin}_x (\|Ux - v\|^2 + \lambda^2 \|x\|^2), \tag{2}$$

where $\lambda^2$ is the ridge parameter that determines the trade-off between the strength of regularization and the resemblance to the specified electric field. The real-time solution to (2) can also be calculated in one matrix-vector multiplication by:

$$x^* = \operatorname{argmin}_x (U^T U + \lambda^2 I)^{-1} U^T v. \tag{3}$$

Figure 3:
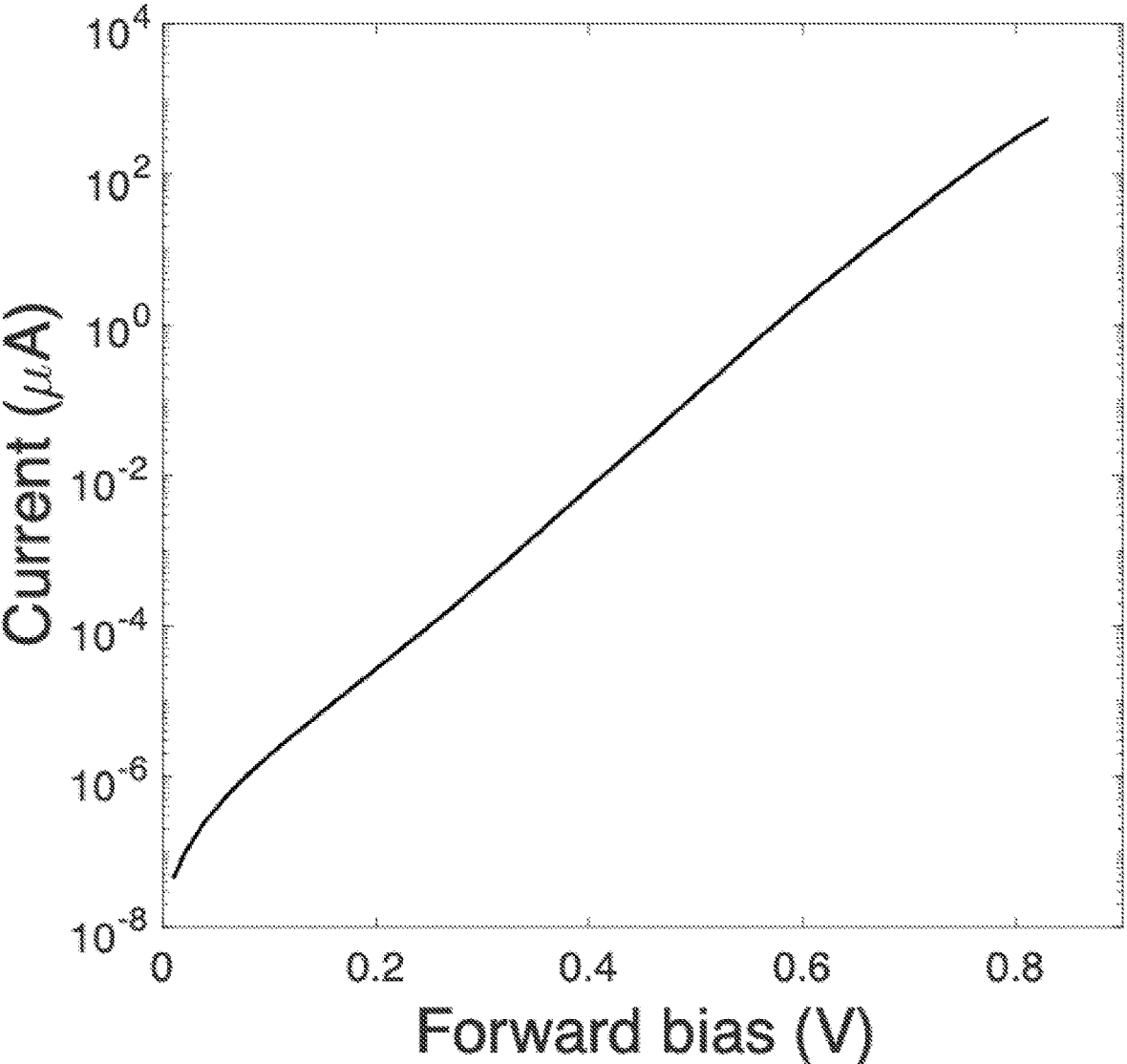
FIG. 3 shows according to an exemplary embodiment of the invention conductivity of the diode increases exponentially with the forward bias.
Figure 4A:
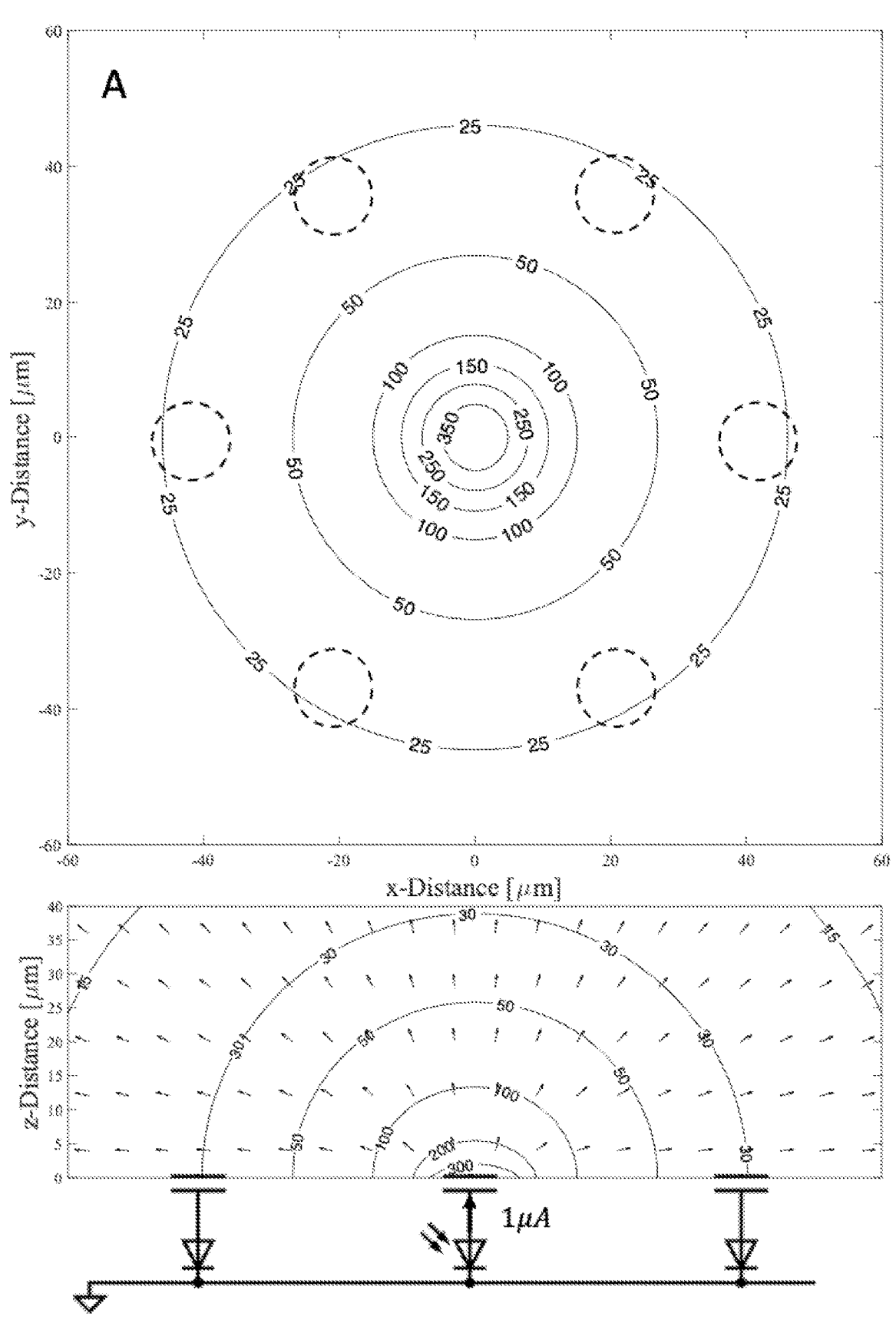
FIGS. 4A-B show according to an exemplary embodiment of the invention computed electric potential above the electrode array in the retina when the center pixel injects 1 μA of anodal current, (FIG. 4A) without preconditioning of the neighboring pixels. Top panel: top-down view of the electrode array surface with the dashed circles indicating the electrodes of the six neighboring pixels. The contour lines show the electric potential in mV, versus a reference electrode placed at a distance. Bottom panel: side view taken at y=0. The arrows indicate the direction of the local current. The circuit diagram schematically shows the photodiodes and the capacitive electrode-electrolyte interfaces of the photovoltaic pixels, with their return electrodes connected together.
Figure 4B:
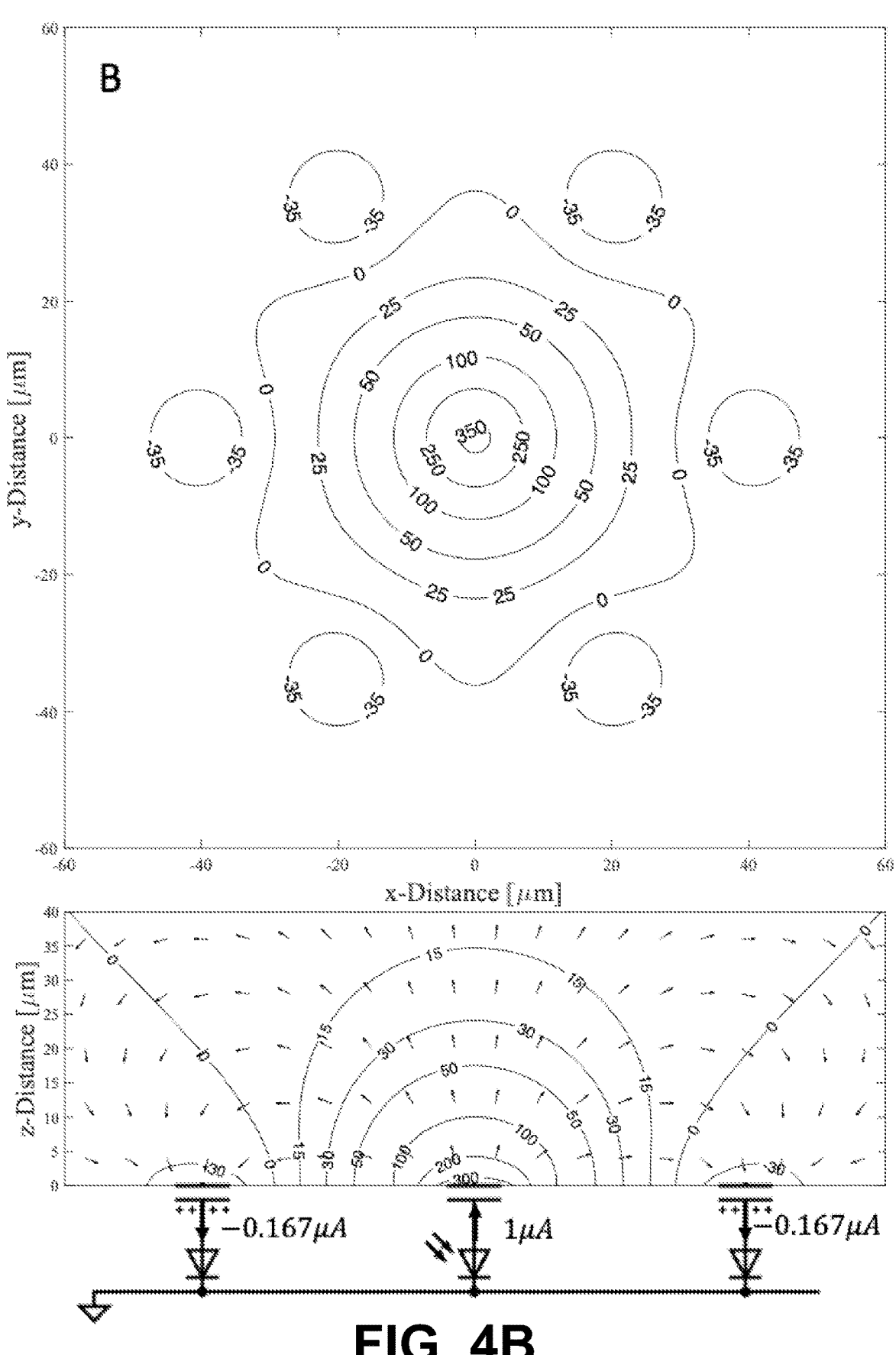
Figure 5:
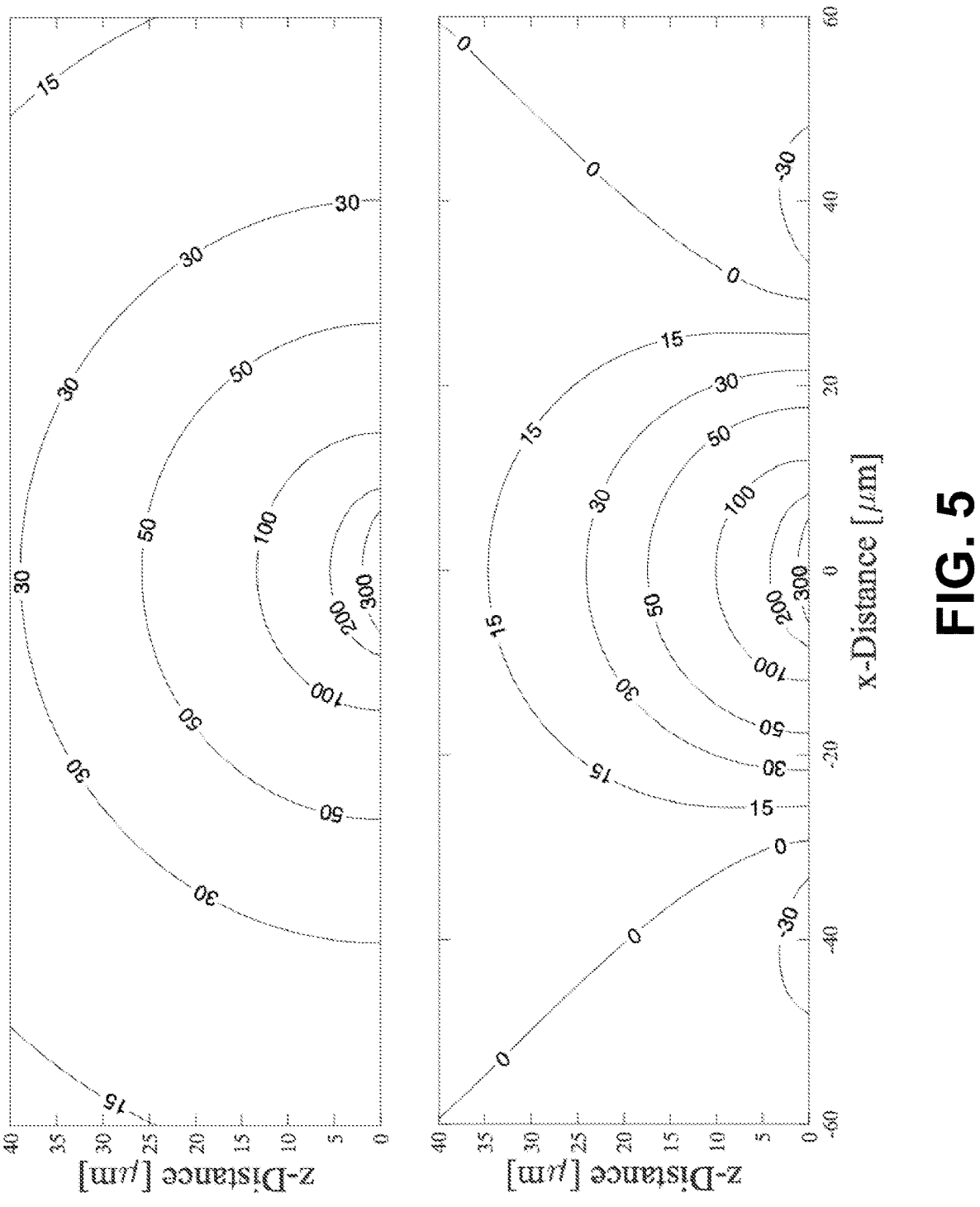
FIG. 5 shows according to an exemplary embodiment of the invention side-by-side comparison of the electric potential without (top panel) and with (bottom panel) preconditioning of the neighboring pixels. Computed electric potential in the medium is calculated when the center pixel injects 1 μA of current. Note much tighter confinement of the electric field in the bottom panel.
Figures 6A, 6B:
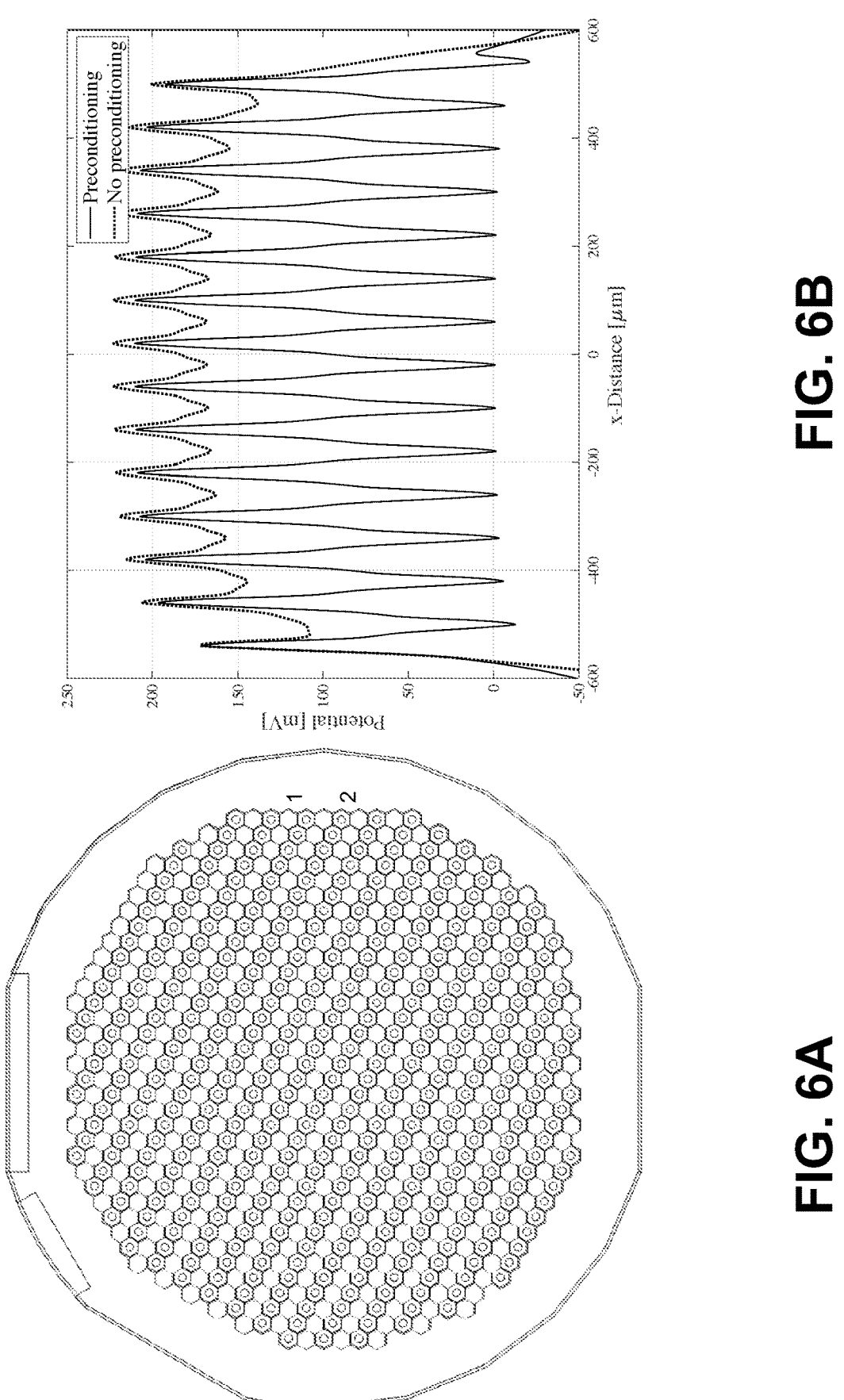
FIGS. 6A-B show according to an exemplary embodiment of the invention in FIG. 6A photovoltaic array with 40 μm pixels illuminated with a grating pattern.

The sequence of the signal processing, pixel preconditioning, and stimulation can be implemented as following: for the typical frame rate of 30 Hz, each frame lasts for about 32 ms. Typical illumination time of the stimulating pixels is between 1 and 10 ms. Once an image frame is acquired by the camera, the sufficiently dark pixels will be designated to serve as the transient returns (for example by thresholding). (1) In the preconditioning phase of the frame, these pixels will be exposed to light at intensities below the stimulation threshold for a sufficient amount of time to accumulate the required charge and become conductive during the stimulation phase of the frame. For a 40 μm wide photovoltaic pixel, the typical range of stimulation current is 0.01 to 1 μA. As shown in FIG. 3, it corresponds to a voltage range of about 0.4 to 0.6 V. Since part of the electric potential above the return pixel during stimulation phase will be provided by the neighboring active pixels, the accumulated voltage on the electrode-electrolyte interface can be lower: 0.2 or 0.3 V. If the photovoltaic pixel includes several diodes in series, this voltage drop is specified per diode. Since the stimulation current density near the electrode should be the same for pixels of all sizes, this voltage range should not depend much on the pixel size. (2) During the stimulation phase, the designated bright pixels are exposed to brighter light with intensity and duration (typically 1-10 ms) corresponding to the desired charge injection, while the dark pixels conduct the current back to the return electrode. With such an arrangement, the stimulation is delayed relative to the image acquisition by no more than one frame period.

Avoidance of stimulation during the preconditioning phase limits the maximum current and hence the maximum charge accumulation for the transient returns, which, at high frame rates, may not be sufficient to enable conduction. An alternative sequence of the signal processing for pixel preconditioning and stimulation can be as following: all pixels remain in low illumination by default, and hence ready for transformation into transient returns. Once an image frame is acquired by the camera, the sufficiently bright pixels will be identified (for example by thresholding). (1) In the preconditioning phase of the frame, these bright pixels will be kept in the dark to let the electrodes discharge, while others continue to be illuminated at the default level. (2) During the stimulation phase, the designated bright pixels will be exposed to brighter light as described above, while the dark pixels will be kept in the dark to sink current as transient returns. With such an arrangement, during the preconditioning phase, current on the pixels designated to become bright is cathodal, and therefore the stimulation threshold is about 5 times higher than during the anodal simulation phase by photocurrent, which should reduce the chances of accidental stimulation. And even if such cathodal stimulation during the preconditioning phase will occur, it should not introduce much confusion since these pixels are supposed to be activated a few ms later by the photocurrent.

The two strategies described above may be combined to balance the minimization of energy with avoidance of unintended stimulation.

Another approach can be based on image multiplexing. With a typical image refresh rate of 30 Hz, each frame lasts about 32 ms. Photovoltaic stimulation pulses typically range from 0.8 to 8 ms, enabling at least 4 pulses during each frame. Therefore, pixels in the image can be divided into 4 groups, activated in sequence. This way, pixels illuminated in the previous group are charged and can serve as local returns for the pixels activated in the next group. Another advantage of this approach is that only ¼ of the pixels is activated simultaneously, and even less than that, if the images are sparse. This greatly reduces the build-up of the electric potential and hence enables better localization of the stimulus. Utilizing the fact that pulse duration varies in various pixels, pixels van be divided in a larger number of groups, or even activated asynchronously.

To speed-up the image processing for determination of the dark pixels for preconditioning and to reduce the delay, the continuity of natural visual input can be exploited to predict the next frame based on the pervious images in the video sequence. For this purpose, predictive tracking algorithms, such as the Kalman filter or exponential smoothing, can be applied.

What is claimed is:

1. A method of providing illumination to a photovoltaic retinal prosthesis, comprising:
    (a) projecting a video stream onto a retinal implant, wherein the retinal implant includes an array of photovoltaic pixels configured to provide retinal stimulus responsive to the video stream, wherein the array of photovoltaic pixels has a common return electrode, wherein each pixel has an active electrode that is coupled to retinal tissue via a capacitive interface or a faradaic interface, and wherein each pixel includes one or more photodiodes connected in series between the common return electrode and the corresponding active electrode; and
    (b) configuring the projected video stream based on a source video stream such that one or more pixels of the retinal implant that will be dark in a next frame of the projected video stream are optically preconditioned by the projected video stream to become sufficiently conductive to act as transient local return electrodes during the next frame of the projected video stream.

2. The method as set forth in claim 1, wherein the transient local return electrodes are preconditioned to reach a bias voltage in a range of 0.2 V to 0.7 V per photodiode by illumination from the projected video stream.

3. The method as set forth in claim 2, wherein the transient local return electrodes are preconditioned to reach the bias voltage in the range of 0.3 V to 0.6 V per photodiode.

4. The method as set forth in claim 1, wherein an image processing duration for pre-conditioning and stimulation is no longer than a frame duration of the source video stream.

5. The method as set forth in claim 1, further comprising a preconditioning algorithm which defines a polarity and an amplitude of the current at each electrode, and is optimized under a minimum-mean-square-error criterion to approximate a target electric field in a biological tissue.

6. A retinal prosthesis system, comprising:
    a near-the-eye display for a video stream projection onto a retinal implant,
        wherein the retinal implant comprises photovoltaic pixels which convert light from the display into an electric current flowing through a biological tissue to stimulate retinal neurons,
        wherein each pixel in the retinal implant comprises one or more photodiodes connected in series between an active electrode and a return electrode,
        wherein the active and return electrodes are coupled to an electrolyte of the biological tissue via a capacitive interface or a faradaic interface,
    wherein the return electrodes of the pixels are connected together, and
    wherein a sequence of images in the video stream projected by the near-the-eye display onto the retinal implant is designed to optically precondition designated pixels to become sufficiently conductive to serve as transient return electrodes by accumulating a bias voltage at an electrode-electrolyte interface in these pixels.

7. The system as set forth in claim 6, wherein the photodiodes are made of crystalline silicon and wherein the bias voltage is in the range of 0.2-0.7 V per photodiode.

8. The system as set forth in claim 6, wherein the bias voltage exceeds 0.3V per photodiode.

9. The system as set forth in claim 6, wherein a penetration depth of an electric field into a retina is optimized for an anatomy of a patient by controlling a distance between illuminated pixels in a current video frame and the pixels preconditioned in previous frames, but not illuminated in the current video frame.

10. The system as set forth in claim 6, wherein the photovoltaic pixels comprise one or more optically controlled transistors to regulate a discharge current.

11. A retinal prosthesis, comprising:

an array of photovoltaic pixels configured to provide retinal stimulus responsive to a received video stream, wherein the array of photovoltaic pixels has a common return electrode, wherein each pixel has an active electrode that is capacitively or faradaically coupled to a retinal tissue, wherein each pixel includes one or more photodiodes connected in series between the return electrode and the corresponding active electrode, and wherein each pixel further includes an optically controllable conductance element, wherein illumination of the array of photovoltaic pixels with a secondary illumination pattern selects one or more pixels of the retinal implant to act as local return electrodes by activating corresponding conductance elements.

\* \* \* \* \*